United States Patent [19]
Petvai et al.

[11] Patent Number: 5,569,328
[45] Date of Patent: Oct. 29, 1996

[54] SILICON SEMICONDUCTOR WAFER TEST

[76] Inventors: Steve I. Petvai, 2 Bell Air La., Wappinger Falls, N.Y. 12590; Michael P. Buet, 2 Mountain View Rd., New Fairfield, Conn. 06812

[21] Appl. No.: 370,318

[22] Filed: Jan. 10, 1995

[51] Int. Cl.$^6$ .................................................. C23C 16/00
[52] U.S. Cl. ..................... 118/696; 118/712; 118/715; 118/719; 436/178; 901/48
[58] Field of Search .................................. 118/715, 719, 118/696, 712; 436/178; 901/48

[56] References Cited

U.S. PATENT DOCUMENTS

| | | | |
|---|---|---|---|
| 3,995,756 | 12/1976 | Hjelm | 901/48 |
| 4,297,908 | 11/1981 | Zimmer | 901/48 |
| 4,990,459 | 2/1991 | Maeda | 436/178 |
| 5,055,413 | 10/1991 | Kageyama | 436/178 |

*Primary Examiner*—Richard Bueker
*Attorney, Agent, or Firm*—David Fink

[57] ABSTRACT

The invention relates to a system for manufacturing semiconductor devices from silicon semiconductor wafers, comprising forming device operable forming a silicon semiconductor wafer, oxidizing device operable for forming an oxidation gate on the silicon semiconductor wafer and thereafter, a testing arrangement for testing the silicon semiconductor wafer for contaminants using a test drop; wherein the improvement comprises, rotating device operable for receiving the wafer and for rotating in one direction and the opposite direction at predetermined rates in response to first electrical signals; carrier device operable for being positioned on the silicon semiconductor wafer and for retaining at least a portion of the test drop in contact with the wafer during relative movements of the carrier device over the surface of the wafer while substantially eliminating direct contact between the carrier device and the wafer; radial moving device operable for moving the carrier device along a predetermined radial path relative any clockwise and counterclockwise rotation of the wafer in response to second electrical signals; first control device operable for generating the first electrical signals for causing the rotating device to rotate first in one direction and then in the opposite direction so that the resultant effect is an incremental rotation of the wafer; and second control device operable for generating second electrical signals for causing the radial moving device to move the carrier device incrementally radially so that the carrier device follows a path covering substantially all of a predetermined portion of the surface of the wafer.

8 Claims, 3 Drawing Sheets

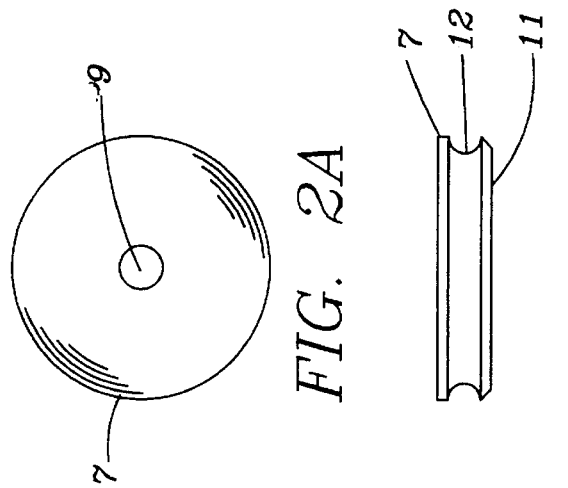
FIG. 2A
FIG. 2B
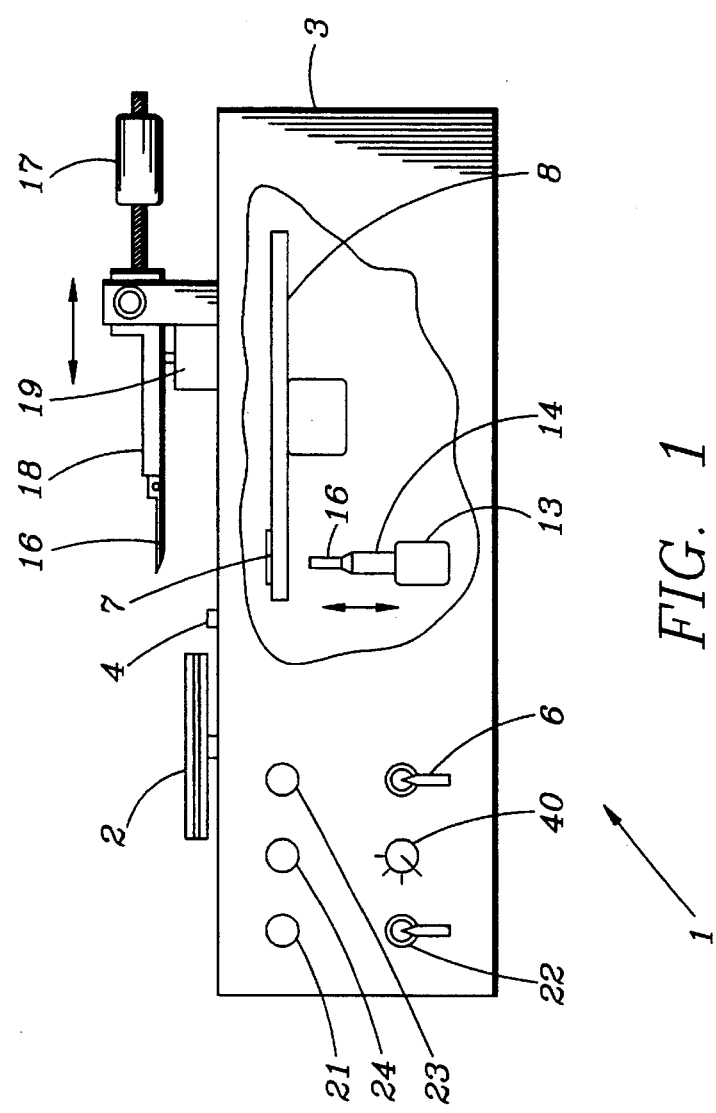
FIG. 1

SILICON SEMICONDUCTOR WAFER TEST

FIELD OF THE INVENTION

The present invention relates to a system and process for testing a silicon semiconductor wafer, and more particularly to testing the wafer for contamination during the manufacturing of semiconductor devices.

BACKGROUND OF THE INVENTION

During the manufacturing of certain silicon semiconductor devices such as MOS type semiconductor devices, the amount of certain contaminants such as heavy metals or particles which may be present when the semiconductor wafer is formed can seriously degrade the performance of the final devices. Despite careful manufacturing procedures, there is a possibility that contaminants may appear in the wafer and may be sufficient to make any devices made from the contaminated wafer useless.

The industry has recognized this problem and it is the accepted practice in the industry to test silicon semiconductor wafers for contaminants after a typical batch of up to 25 or more have been made and have been partially processed. One of the wafers in the batch is used for tests and is then discarded. The remaining wafers are further processed only if the tested wafer provides satisfactory data.

The contaminants in a silicon semiconductor wafer are present on or in the silicon substrate prior to gate oxidation which is one of the production operations. The contaminants become or tend to become incorporated into the silicon oxide as it is being formed. Typically, the silicon oxide layer is about 500 Angstroms thick and this layer will decrease in thickness during additional operations.

The test for contaminants in a silicon semiconductor wafer according to the prior art is carried out on the test wafer after the batch of wafers including the test wafer has been subjected to gate oxidation. The test wafer is separated from the batch and is subjected to hydrofluoric acid fumes (HF) in a chamber to etch away the oxide layer. The movement of the test wafer is performed by an operator, thereby increasing the possibility of further contamination. Thereafter, the procedure is to perform a "liquid drop test". As used herein, the "liquid drop test" refers to a test sometimes referred to in the industry as the "Toshiba Process" in which a predetermined quantity of a liquid solution usually comprising hydrofluoric acid and certain other components (hereinafter, the "test drop") is deposited on the test wafer on the side from which the oxide layer had been removed and the test wafer is manually manipulated to cause the movement of the test drop relative the surface of the test wafer so that the test drop contacts substantially every portion of the surface of the test wafer on that side.

The test drop is removed by pouring it into a cup and subjected to tests to determine the presence of contaminants so that a decision can be made as to the entire batch. The specific components of the test drop are usually regarded by companies as proprietary and these components can vary depending on the specific manufacturing process and the manufacturing materials being utilized.

The repeatability and reliability of the prior art procedure for the liquid drop test depends entirely on the mechanical skill of the person moving the test drop over the surface of the test wafer. Preferably, the test drop should contact every portion of the surface and the contact time at each portion should be approximately the same. The total time required by the manual manipulation of the test drop over the surface of the test wafer must be sufficient to provide assurance that the test drop has been maneuvered over the entire surface. Thus, any attempt to minimize the time for this procedure creates a risk of an unreliable movement of the test drop over the surface of the test wafer as well as unequal time of the test drop over the surface of the test wafer.

It can be seen that a need exists for a reliable and repeatable method and system for conducting the liquid drop test for silicon semiconductor wafers. In addition, there is a great need for a semi-automated and preferably a fully automated system for moving a test wafer into a testing position, conducting the liquid drop test, and thereafter, removing and analyzing the liquid drop for the presence of contaminants.

SUMMARY OF THE INVENTION

The present invention overcomes the disadvantages of the prior art problems by providing a system and process for conducting the testing of a silicon semiconductor wafer for contaminants reliably and repeatably which is much faster than the prior art and suitable or either semi- or fully-automated operations.

As used herein, a "silicon semiconductor wafer" refers to a basic substrate known and used in the industry for the production of semiconductor devices. In addition, as used herein, "gate oxidation" and "silicon oxide layer" are used consistent with the meaning in the prior art.

It is an object of the invention to provide a repeatable and reliable equivalent to the liquid drop test.

It is a further object of the invention to provide a repeatable and reliable equivalent to the liquid drop test which is faster than the prior art procedure for the liquid drop test.

It is a yet another object of the invention to provide a repeatable and reliable equivalent to the liquid drop test which is at least semi-automated and is suitable for being fully-automated for production line use.

It is still another object of the invention to provide a system which allows the selective testing of a predetermined area of a wafer to provide information for the identification of a potential source of contaminants during the processing of the wafer.

In one broad embodiment, the invention relates to a system for manufacturing semiconductor devices from silicon semiconductor wafers, comprising forming means operable forming a silicon semiconductor wafer, oxidizing means operable for forming an oxidation gate on the silicon semiconductor wafer and thereafter, a testing arrangement for testing the silicon semiconductor wafer for contaminants using a test drop; wherein the improvement comprises, rotating means operable for receiving the wafer and for rotating in one direction and the opposite direction at predetermined rates in response to first electrical signals; carrier means operable for being positioned on the silicon semiconductor wafer and for retaining at least a portion of the test drop in contact with the wafer during relative movements of the carrier means over the surface of the wafer while substantially eliminating direct contact between the carrier means and the wafer; radial moving means operable for moving the carrier means along a predetermined radial path relative any clockwise and counterclockwise rotation of the wafer in response to second electrical signals; first control means operable for generating the first electrical signals for causing the rotating means to rotate first in one direction and then in the opposite direction so that the resultant effect is an incremental rotation of the wafer; and second control means operable for generating second electrical signals for causing the radial moving means to move the carrier means incrementally radially so that the carrier means follows a path covering substantially all of a predetermined portion of the surface of the wafer.

Another embodiment of the invention also includes provisions for moving the carrier means in a predetermined pattern near the center of the wafer.

In yet another embodiment, the invention starts the movement of the carrier means from near the circumference and has it move radially towards the center of the wafer in increments about equal to half the width of the carrier means.

In still another embodiment, the invention features the first control means generating first electrical signals for causing the rotation of the wafer so that the relative rate of movement of the carrier means with respect to the wafer is approximately equal to a predetermined value.

In a preferred embodiment, the invention operates to collect data from substantially the entire surface of the wafer.

In another broad embodiment, the invention relates to a process for manufacturing semiconductor devices from silicon semiconductor wafers, comprising forming a silicon semiconductor wafer, forming an oxidation gate on the silicon semiconductor wafer and thereafter, testing the silicon semiconductor wafer for contaminants using a test drop; wherein the improvement comprises, providing carrier means operable for being positioned on the silicon semiconductor wafer and for retaining at least a portion of the test drop in contact with the wafer during relative movements of the carrier means over the surface of the wafer while substantially eliminating direct contact between the carrier means and the wafer; and moving the carrier means over path covering substantially all of a predetermined portion of the surface of the wafer.

Preferably, the movement of the carrier means is incremental radially and in one direction and then the opposite direction so that the relative rate of movement of the carrier means with respect to the wafer is approximately equal to a predetermined value.

Preferably, the movement of the carrier means starts near the circumference and moves towards the center of the wafer.

Other embodiments, features and advantages if the invention will become apparent upon reading the specification.

BRIEF DESCRIPTION OF THE DRAWINGS

FIG. 1 is a side elevational view of a semi-automatic system incorporating the invention with a portion removed to show interior elements.

FIGS. 2A and 2B are plan and elevational views, respectively, of a carrier according to the invention.

DETAILED DESCRIPTION OF THE PREFERRED EMBODIMENTS

Figure 3:
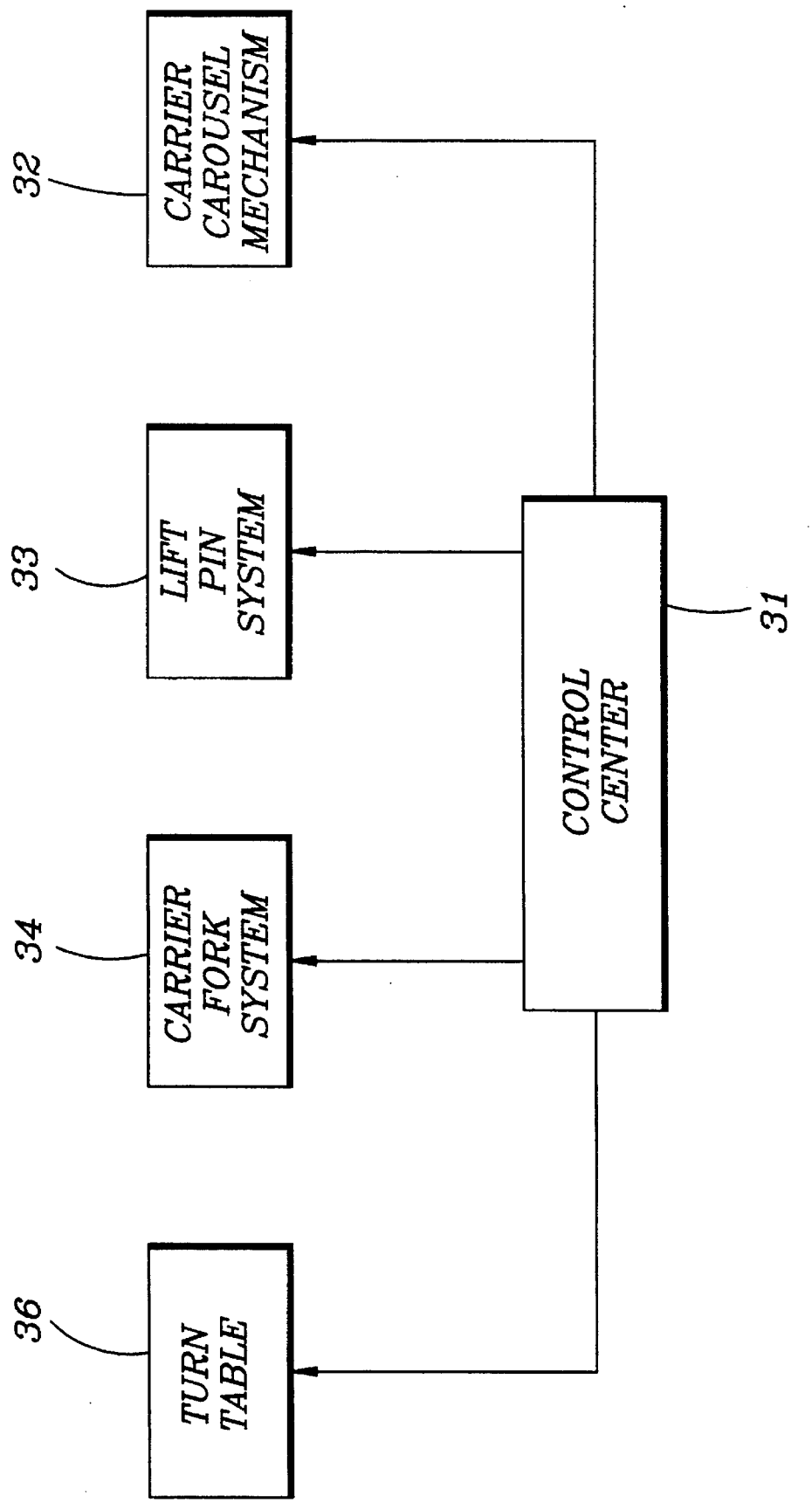
FIG. 3 shows a block diagram of the electronic system for controlling the mechanical operations of the system shown in FIG. 1.

FIG. 1 shows a semi-automatic system 1 according to the invention. A wafer (not shown) is placed on a rotatable table 2 which includes a vacuum chuck for retaining the wafer in position above system cabinet 3. The vacuum chuck is widely used in the industry for holding and/or retaining a wafer and the like in a predetermined position or for use in holding a wafer when it is being transported or moved from one location to another location. The table 1 includes adjustments for maintaining a wafer so that its upper surface is substantially level. Two stops or pins 4 may be used to assist in positioning the wafer on the table 2. It is convenient to have the pins 4 retractable so that after the wafer is positioned the pins 4 can be retracted to the position shown in the FIG. 1 or, preferably, below the surface of the cabinet 3 of the system. Switch 6 operates the vacuum chuck of the table 2.

After a wafer has been positioned on the table 2, a carrier means such as liquid drop carrier 7 must be brought to the wafer. A carousel 8 has carriers 7 positioned around its periphery so that each time a wafer is to be tested a new carrier 7 can be rotated into a position for use such as the carrier 7 shown in the FIG. 1.

FIGS. 2A and 2B show a suitable carrier 7. The carrier 7 is preferably made from a substance which is relatively light and substantially non-reactive with hydrofluoric acid such as quartz. Generally, the outside diameter can be about 19 mm and the opening 9 can have a diameter of about 8 mm. The outside diameter of the bottom 11 can be about 14 mm. There is a groove 12 defined around the periphery for use in holding and moving the carrier 7 as will be disclosed herein. The overall height of the carrier 7 is about 3 mm.

As shown in FIG. 1, a lift pin mechanism 13 operates carrier lift pin 14 to raise it up from the position shown so that pin 16 engages the opening 9 of the carrier 7 and positions the carrier 7 with respect to carrier fork 16 for engagement by the carrier fork 16. The carrier carousel 8 is designed to allow the desired movement of the carrier lift pin 14 upward. The carrier fork 16 is operated to engage the carrier 7 and counterweight 17 is positioned to balance translating arm mechanism 18 after the carrier 7 has been engaged. The counterweight 17 also acts to minimize the pressure the carrier 7 will have on a wafer during the test. Arm lift solenoid actuator 19 lifts the carrier fork 16 up against a stop not shown to a predetermined height adjusted so that the carrier fork 16 can be moved towards the carrier 7 on the lift pin mechanism 13 for engagement with the carrier 7. The carrier fork 16 contacts the carrier 7 and pushes into the carrier 7 until the carrier fork 16 engages the groove 12. The positioning of these components and relative movement is carefully determined for achieving this result. The loading of the carrier 7 is activated by load switch 21. The arm lift solenoid actuator 19 is operated by switch 22.

The position of the table 1 is brought to a predetermined position for the start of the operations by home switch 23 while start switch 24 starts the operation of the process according to the invention. The home switch 23 positions the table 1 as well as retracting the translating arm mechanism 18 and initializing the logic of the system for the operations of the invention.

After the carrier 7 has been loaded into the carrier fork 16, the translating arm mechanism 18 is rotated to position the carrier 7 over the outer edge of a wafer on the table 1. A predetermined amount of a suitable liquid is introduced into the carrier 7. The suitable liquid includes hydrofluoric acid and other components as is known in the art. The liquid can vary depending on the property being tested and could have some proprietary aspects. The liquid is introduced using a pipette not shown. This causes the carrier 7 to move downward towards the wafer. The shape of the carrier 7 is such that the liquid tends to adhere to the carrier 7 during the process of the invention. The carrier 7 is preferably spaced apart from the wafer by the liquid during the process. The amount of the liquid can be determined experimentally so that throughout the process substantially all of the liquid follows the movement of the carrier 7.

Other variation is the shape and design of the carrier 7 can be used consistent with the goals and spirit of the invention. Accordingly, the carrier 7 could be other than round, it could be without a central hole, and it could have other physical variations as long as the carrier 7 tends to retain the liquid as the carrier 7 moves relative the wafer and the carrier 7 tends to be spaced apart from the wafer by the liquid during the movement.

FIG. 3 shows a simplified block diagram for operating the main components of the system shown in FIG. 1. A control center 31 is connected to a carrier carousel mechanism subsystem 32, lift pin subsystem 33, carrier fork subsystem, and table subsystem 36. The subsystems operate in accordance with the operations disclosed herein and are designed using well known techniques. The subsystem 32 controls the carrier carousel mechanism 8. The subsystem 33 controls lift pin mechanism 13. The subsystem 34 controls carrier fork 16. The subsystem 36 controls the table 2. These subsystems as well as the other components of the invention utilize readily available technology and commercially available parts so that the electro-mechanical system can be assembled without undue experimentation.

The subsystem 36 rotates the table 1 first in one direction and then the opposite direction in a predetermined manner so that the overall result is progressive rotation in one direction. That is, the wafer on the table 1 will effectively be rotated around progressively in one direction. In one preferred arrangement, the table 1 is rotated in three steps in one direction and then rotated back one step. The rotation can also be two steps in one direction and one step in the opposite direction. Preferably, the rate of rotation of the table 1 is coordinated to the radial position of the carrier 7 on the wafer so that the rotational velocity of the carrier 7 relative to the wafer is about constant. By maintaining a generally constant speed over the wafer, each portion of the wafer is subjected to the same exposure to the liquid on the carrier 7. The highest rate of rotation is less than a rate which could cause the liquid on the carrier 7 to become separated from the carrier 7. The rate of effective rotation of table 1 is determined by switch 40 which can provide a continuous change from off to a predetermined high speed or predetermined steps of off, low, medium and high speed.

For one embodiment, after each rotation of the wafer on the table 1 a predetermined amount slightly greater than 360°, the translating arm mechanism 18 moves the carrier 7 from its radial position towards the center of the wafer about the width of the carrier 7. This action is repeated until the carrier 7 is about at the center of the wafer 7, typically about 10 mm from the center. The action of the movement changes so that the wafer remains stationary and the translating arm mechanism 18 moves back and forth about 15 mm a predetermined number of times, for example, twice. The liquid is removed from the carrier 7 using a pipette and tested in accordance with known technology.

The system shown in FIG. 1 can be operated differently to obtain data overlooked in the prior art. During the formation of a wafer, various chemicals and processing components interact with the wafer. It is possible that one or more of these components may be the source of contaminants and the cost for unusable wafers may be high until the source of the problem has been identified. A modified liquid drop test can be conducted with the invention in which a predetermined portion of the surface of the wafer is subjected to the liquid drop or the surface is tested in a predetermined pattern. This is now possible because the positioning of the carrier 7 which is moving the liquid on the wafer is under the precise control of the electronic system which controls the rotation of the table 1 and the radial position of the translating arm mechanism 18. Accordingly, the control center 31 can be used for this purpose. This partial testing can utilize the index marking of wafers in practice in the art to relate a portion for testing of the wafer to the components interacting with the wafer during its formation.

Figure 4:
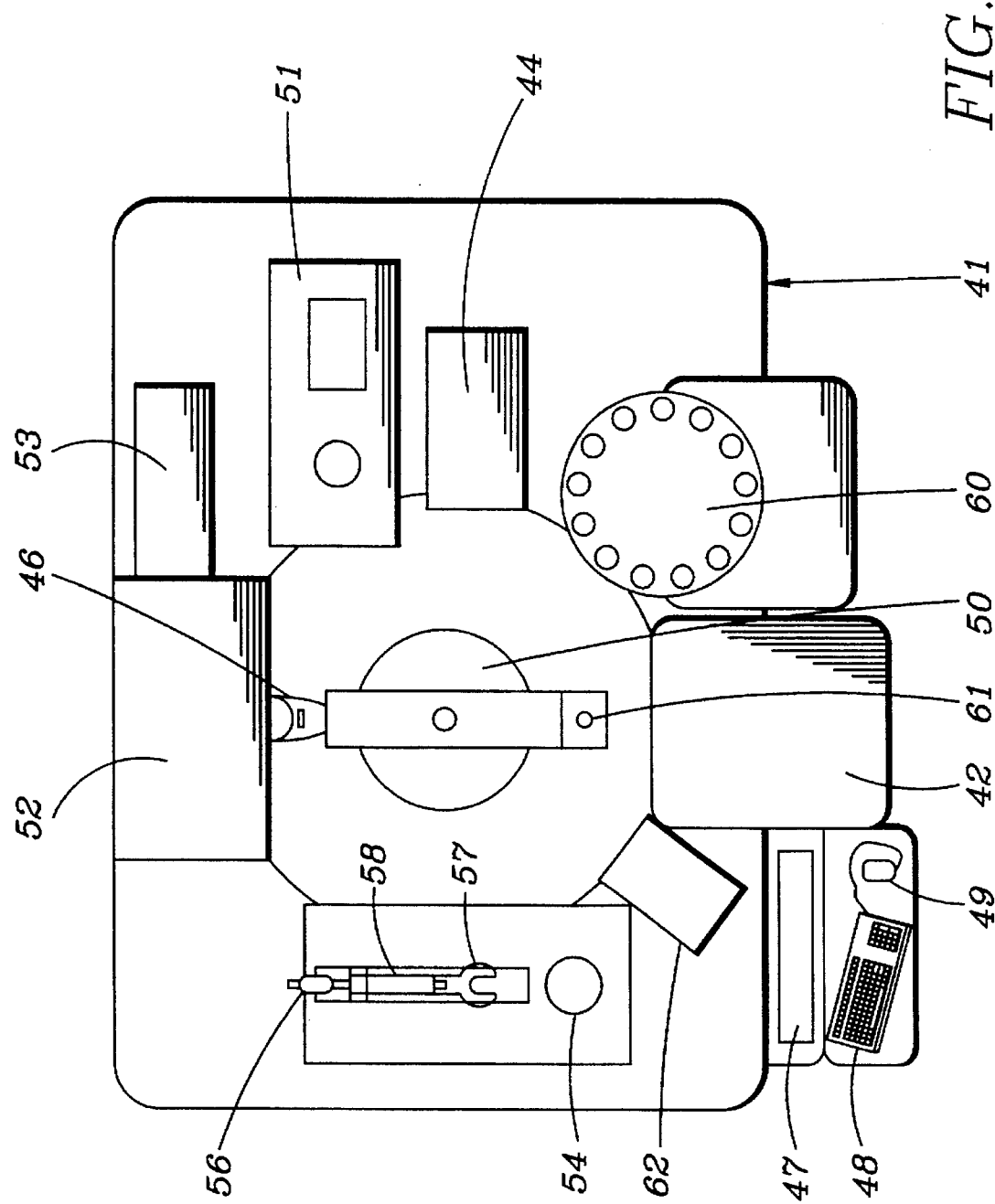
FIG. 4 is a plan view of an automatic system incorporating the invention.

Turning now to FIG. 4, a fully automated system 41 enables the complete testing of a wafer according to the invention. The system 41 defines a Class 1 environment in accordance with the art with a cover and access openings not shown to simplify the figure. A small machine interface (SMIF) container 42 is used to transport wafer cassette stand 44 from a Class 10 production area in a closed container to the Class 1 environment with the batch of wafers to be tested stored inside of it. The container 42 is opened after it is in the Class 1 environment and the wafer cassette stand 44 is moved to the position shown in FIG. 4. A wafer not shown is selected for testing from the wafer cassette stand 44 using a wafer vacuum pick-up fork 46 under the control of a computer system 47 which is commanded by keyboard 48 and mouse 49. A robotic control 50 interfaces between the computer system 47 and the pick-up fork 46. The movement of the pick-up fork 46 can be automated to be robotic through the use of visual sensors using techniques known in the prior art. The pickup fork 46 moves the wafer to bar code reader 51 so that the wafer being tested can be identified in accordance with commercial practice. The pick-up fork 46 rotates and delivers the wafer to chamber 52 where the wafer is subjected to etching with hydrofluoric acid to remove the oxide layer. An exhaust scrubber 53 is connected to the chamber 52 to treat the exhaust fumes appropriately.

After treatment in chamber 52, the wafer is retrieved by the pick-up fork 46 and positioned on a vacuum table 54 for the liquid drop testing either partially or completely. Counterweight 56 balances carrier fork 57 which is on translating arm mechanism 58. A carrier delivery operation such as described in connection with FIG. 1 is used in FIG. 4 so that the carrier not shown can be positioned adjacent to the wafer to receive liquid for the test.

A liquid cup carousel 60 has premeasured amounts of the liquid to be used. A liquid handler 61 opposite the pick-up fork 46 is rotated to retrieve liquid from one of the compartments of the carousel 60. The liquid handler 61 then rotates to a position near the carrier held by the carrier fork 57 and dispenses the liquid. After the test has been completed, the liquid handler 61 is used to extract the liquid from the carrier on the tested wafer and the liquid is deposited in the compartment on the carousel 60 for testing in accordance with industry standards. The system 41 can be further automated to deliver the liquid after the wafer test to a port which will carry out the tests on the liquid automatically.

The computer system 47 can be used to program the movement of the carrier fork 57 to cover the entire surface or a selected portion of the surface of a wafer as described with respect to the operation of the system 1 shown in FIG. 1. In general, the movement of the carrier fork 57 is similar to the movement of the carrier fork 16 with movement first in one direction and then the opposite direction.

After the testing of the wafer, the pick-up fork 46 removes the tested wafer and places it in wafer cassette stand 62. Then, another wafer is selected from the wafer cassette stand 44 for testing.

There has been described a novel system and process. It is evident that those skilled in the art may now make numerous uses and modifications of and departures from the specific embodiments described herein without departing from the inventive concepts. Consequently, the invention is to be construed as embracing each and every feature and novel combination of features present or possessed by the system and process herein disclosed and limited solely by the spirit and scope of the appended claims.

What is claimed is:

1. A system for manufacturing semiconductor devices from silicon semiconductor wafers, comprising forming means operable forming a silicon semiconductor wafer, oxidizing means operable for forming an oxidation gate on the silicon semiconductor wafer and thereafter, a testing arrangement for testing the silicon semiconductor wafer for contaminants using a liquid test drop; wherein the improvement comprises, rotating means operable for receiving the wafer and for rotating in one direction and the opposite direction at predetermined rates in response to first electrical signals; carrier means operable for being positioned on said silicon semiconductor wafer and for retaining at least a portion of the test drop in contact with said wafer during relative movements of said carrier means over the surface of said wafer while substantially eliminating direct contact between said carrier means and said wafer; said carrier means comprising a disk like object having a generally centrally located hole for receiving said test drop, radial moving means operable for moving said carder means along a predetermined radial path relative any clockwise and counterclockwise rotation of said wafer in response to second electrical signals; said radial moving means comprising balancing means coupled to said object, said balancing means operable to provide a counterbalance, to said object so that said object is positioned above said wafer by a portion of said test drop; first control means operable for generating said first electrical signals for causing said rotating means to rotate first in one direction and then in the opposite direction so that the resultant effect is an incremental rotation of said wafer; and second control means operable for generating second electrical signals for causing said radial moving means to move said carrier means incrementally radially so that said carrier means follows a path covering substantially all of a predetermined portion of the surface of said wafer.

2. The system as claimed in claim 1, wherein said portion of the surface is substantially all of the surface.

3. The system as claimed in claim 1, wherein said rotating means rotates at a rate related to the position of said carrier means so that the relative rate of movement of said carrier means with respect to said wafer is approximately the same as a predetermined value.

4. The system as claimed in claim 1, wherein said first and second control means are operable for stopping the rotation of said wafer when said carrier means has reached a predetermined position near the center of said wafer and thereafter, moving said carrier means back and forth along a linear path a predetermined distance.

5. The system as claimed in claim 1, wherein said rotating means operates to rotate said carrier means at least about 360° with respect to said wafer and said radial moving means operates to move said carrier means towards the center of said wafer approximately the width of said carrier means and this relationship is repeated until said carrier means reaches a predetermined radial position with respect to the center of said wafer.

6. The system as claimed in claim 1, wherein the operations are carried out as part of an automated operation comprising a robotic means to supply said carrier means, position said carrier means on said wafer, and control said first and second control means.

7. The system as claimed in claim 1, wherein said carrier means is shaped with an annular opening to retain the liquid during the movement of said wafer.

8. The system as claimed in claim 1, wherein said rotating means includes adjustments for positioning said wafer so that its upper surface is substantially level.

* * * * *